United States Patent
Baruch et al.

(10) Patent No.: US 6,463,187 B1
(45) Date of Patent: Oct. 8, 2002

(54) VARIABLE COUPLER FIBEROPTIC SENSOR AND SENSING APPARATUS USING THE SENSOR

(75) Inventors: Martin C. Baruch, Charlottesville; Charles Adkins, Earlysville; David Gerdt, North Garden, all of VA (US)

(73) Assignee: Empirical Technologies Corporation, Charlottesville, VA (US)

( * ) Notice: Subject to any disclaimer, the term of this patent is extended or adjusted under 35 U.S.C. 154(b) by 0 days.

(21) Appl. No.: 09/316,143

(22) Filed: May 21, 1999

Related U.S. Application Data

(60) Provisional application No. 60/097,618, filed on Aug. 24, 1998, and provisional application No. 60/126,339, filed on Mar. 26, 1999.

(51) Int. Cl.[7] .................................................. G02B 6/00
(52) U.S. Cl. ........................... 385/12; 385/13; 385/31; 385/32; 385/39
(58) Field of Search .......................... 385/12–13, 32.31, 385/43.39, 46; 600/528

(56) References Cited

U.S. PATENT DOCUMENTS

| | | | |
|---|---|---|---|
| 4,245,648 A | 1/1981 | Trimmer et al. ............. 128/680 |
| 4,545,253 A | 10/1985 | Avicola ........................ 73/655 |
| 4,634,858 A | * 1/1987 | Gerdt et al. ................. 250/227 |
| 4,862,144 A | 8/1989 | Tao .............................. 340/573 |
| 4,947,859 A | 8/1990 | Brewer et al. ............... 128/715 |
| 5,026,984 A | 6/1991 | Gerdt ...................... 250/227.21 |
| 5,056,884 A | * 10/1991 | Quinlan, Jr. ................. 385/13 |
| 5,074,309 A | * 12/1991 | Gerdt ........................... 600/528 |
| 5,136,669 A | 8/1992 | Gerdt ........................... 385/39 |
| 5,173,747 A | 12/1992 | Boiarski et al. ............. 356/361 |
| 5,187,366 A | 2/1993 | Hopenfeld ................... 250/302 |
| 5,200,615 A | 4/1993 | Hopenfeld ................... 250/302 |
| 5,222,165 A | * 6/1993 | Bohlinger ..................... 385/16 |
| 5,289,256 A | 2/1994 | Gramling ..................... 356/345 |
| 5,303,586 A | 4/1994 | Zhao et al. .................... 73/293 |
| 5,333,217 A | 7/1994 | Kossat .......................... 385/32 |
| 5,340,715 A | 8/1994 | Slovacek et al. ............... 435/6 |
| 5,343,037 A | 8/1994 | Berkcan ................. 250/227.21 |
| 5,362,971 A | 11/1994 | McMahon et al. .......... 250/577 |
| 5,378,889 A | 1/1995 | Lawrence ............. 250/227.16 |
| 5,394,239 A | 2/1995 | Valette ........................ 356/345 |
| 5,481,922 A | 1/1996 | Washabaugh ................. 73/774 |
| 5,494,798 A | 2/1996 | Gerdt et al. .................... 435/6 |
| 5,525,800 A | 6/1996 | Sanghera et al. ....... 250/339.08 |
| 5,532,493 A | 7/1996 | Hale et al. ............... 250/458.1 |
| 5,535,747 A | 7/1996 | Katakura et al. ...... 128/660.02 |
| 5,649,543 A | 7/1997 | Hosaka et al. |
| 5,671,191 A | 9/1997 | Gerdt .......................... 367/140 |
| 5,684,460 A | 11/1997 | Scanlon ....................... 340/573 |
| 5,699,461 A | * 12/1997 | Minemoto et al. ............ 385/12 |
| 5,712,934 A | 1/1998 | Johnson ........................ 385/12 |
| 5,828,798 A | 10/1998 | Hopenfeld ................... 385/12 |

OTHER PUBLICATIONS

Tatterson, Kathleen G., "Optical Acoustic Sensors Could Aid Diagnoses", *Photonics Spectra*, Oct. 1997, pp. 55–56.

* cited by examiner

*Primary Examiner*—Rodney Bovernick
*Assistant Examiner*—Juliana K. Kang
(74) *Attorney, Agent, or Firm*—Miles & Stockbridge P.C.

(57) ABSTRACT

A variable coupler fiberoptic sensor utilizes a coupler having a fused coupling region that can be deflected to change the light distribution to a plurality of output fibers without putting the coupling region under tension. A compact, rugged, and highly sensitive sensor design is achieved by use of a coupler having a fused coupling region arranged substantially in a U-shape to allow the input and output fiberoptic leads to extend from the same side of the sensor structure.

52 Claims, 6 Drawing Sheets

VARIABLE COUPLER FIBEROPTIC SENSOR AND SENSING APPARATUS USING THE SENSOR

CROSS-REFERENCE TO RELATED APPLICATIONS

This application claims the benefit of U.S. Provisional Application Nos. 60/097,618 filed Aug. 24, 1998, and 60/126,339 filed Mar. 26, 1999, both of which are incorporated herein by reference.

The U.S. Government has a paid-up license in this invention and the right in limited circumstances to require the patent owner to license others on reasonable terms as provided for by the terms of Grant No. DAMD17-96-C6035 awarded by the Advanced Research Projects Agency (ARPA).

BACKGROUND OF THE INVENTION

The present invention relates to improved designs for variable coupler fiberoptic sensors and to sensing apparatus using the improved sensor designs.

Variable coupler fiberoptic sensors conventionally employ so-called biconical fused tapered couplers. Such couplers are manufactured by a draw and fuse process in which a plurality of optical fibers are stretched (drawn) and fused together at high temperature. The plastic sheathing is first removed from each of the fibers to expose the portions for forming the fusion region. These portions are juxtaposed, usually intertwisted one to several twists, and then stretched while being maintained above their softening temperature in an electric furnace or the like. As the exposed portions of the fibers are stretched, they fuse together to form a narrowed waist region—the fusion region—that is capable of coupling light between the fibers. During the stretching process, light is injected into an input end of one of the fibers and monitored at the output ends of each of the fibers to determine the coupling ratio. The coupling ratio changes with the length of the waist region, and the fibers are stretched until the desired coupling ratio is achieved—typically by a stretching amount at which the respective fiber light outputs are equal. The coupler is drawn to such an extent that, in the waist region, the core of each fiber is effectively lost and the cladding may reach a diameter near that of the former core. The cladding becomes a new "core," and the evanescent field of the propagating light is forced outside this new core, where it envelops both fibers simultaneously and produces the energy exchange between the fibers. A detailed description and analysis of the biconical fused tapered coupler has been given by J. Bures et al. in an article entitled "Analyse d'un coupleur Bidirectional a Fibres Optiques Monomodes Fusionnes", Applied Optics (Journal of the Optical Society of America), Vol. 22, No. 12, Jun. 15, 1983, pp. 1918–1922.

Biconical fused tapered couplers have the advantageous property that the output ratio can be changed by bending the fusion region. Because the output ratio changes in accordance with the amount of bending, such couplers can be used in virtually any sensing application involving motion that can be coupled to the fusion region.

Conventional variable coupler fiberoptic sensors have relied upon designs in which the fiberoptic coupler is pulled straight, secured under tension to a plastic support member and, in the resulting pre-tensioned linear (straight) form, encapsulated in an elastomeric material such as silicone rubber. The encapsulant forms a sensing membrane that can be deflected by external forces to cause bending of the coupler in the fusion region. The bending of the fusion region results in measurable changes in the output ratio of the coupler. The displacement of the membrane can be made sensitive to as little as one micron of movement with a range of several millimeters.

FIG. 1 of the accompanying drawings illustrates the basic principles of a sensing apparatus including a variable coupler fiberoptic sensor 10 as described above. In the form shown, the sensor 10 includes a 2×2 biconical fused tapered coupler 11 produced by drawing and fusing two optical fibers to form the waist or fusion region 13. Portions of the original fibers merging into one end of the fusion region become input fibers 12 of the sensor, whereas portions of the original fibers emerging from the opposite end of the fusion region become output fibers 14 of the sensor. Reference numbers 18 denote the optical fiber cores. The fusion region 13 is encapsulated in an elastomeric medium 15, which constitutes the sensing membrane. The support member is not shown in FIG. 1.

In practice, one of the input fibers 12 is illuminated by a source of optical energy 16, which may be an LED or a semiconductor laser, for example. The optical energy is divided by the coupler 11 and coupled to output fibers 14 in a ratio that changes in accordance with the amount of bending, of the fusion region as a result of external force exerted on the sensing membrane. The changes in the division of optical energy between output fibers 14 may be measured by two photodetectors 17 which provide electrical inputs to a differential amplifier 19. Thus, the output signal of differential amplifier 19 is representative of the force exerted upon medium 15. It will be appreciated that if only one of the input fibers 12 is used to introduce light into the sensor, the other input fiber may be cut short. Alternatively, it may be retained as a backup in the event of a failure of the primary input fiber. It should be noted that, for simplicity, the coupler 11 is shown without the aforementioned fiber twisting in the fusion region. Such twisting is ordinarily preferred, however, to reduce lead sensitivity, which refers to changing of the output light division in response to movement of the input fiber(s).

Because variable coupler fiberoptic sensors can be made entirely from dielectric materials and optically coupled to remote electronics, they are particularly advantageous for applications in which the presence of electrically conductive elements at the sensor location would pose the risk of electrical shock, burns, fire, or explosion. In the medical field, for example, variable coupler fiberoptic sensors have been proposed for monitoring patient heartbeat during MRI examinations. See U.S. Pat. No. 5,074,309 to Gerdt, which discloses the use of such sensors for monitoring cardiovascular sounds including both audible and sub-audible sounds from the heart, pulse, and circulatory system of-a patient. The use of sensing devices having metallic components in an MRI environment has been known to cause severe burning of patients due to the presence of strong radio frequency fields.

Other applications of variable coupler fiberoptic sensors can be found in U.S. Pat. No. 4,634,858 to Gerdt et al. (disclosing application to accelerometers), U.S. Pat. No. 5,671,191 to Gerdt (disclosing application to hydrophones), and elsewhere in the art.

As compared with other types of fiberoptic sensors, the described variable coupler sensors offer a uniquely advantageous combination of low cost, relatively simple construction, high performance (e.g., high sensitivity and wide dynamic range), and versatility of application. Other known fiberoptic sensors have used such principles as microbending loss, light phase interference, and polarization rotation by means of birefringence. Fiberoptic microbending sensors are designed to sense pressure by excluding light from the fiber in proportion to the changes in pressure. The output light intensity decreases with increases in measured pressure, as pressure is transduced into light loss. Because the measurement accuracy is reduced at lower light levels, the dynamic range of such sensors is severely limited. Interferometric fiberoptic sensors measure changes in pressure by applying pressure to an optical fiber to change its index of refraction. This results in a phase delay that is measured by utilizing a Mach-Zehnder or Michaelson interferometer configuration. These sensors are extremely expensive and require sophisticated modulation techniques that render them unsuitable for many applications. Polarization varying fiberoptic sensors alter the polarization state of a polarized optical signal in accordance with a change in temperature or pressure; Such polarized light sensors require special optical fiber and expensive polarizing beam splitters.

Despite their advantages, variable coupler fiberoptic sensors have been subject to certain limitations inherent in the conventional pre-tensioned linear (straight) coupler design. The conventional design imposes, among other things, significant geometrical limitations. In particular, the size of the sensor must be sufficient to accommodate the fiberoptic leads at both ends of the sensor. The fiberoptic lead arrangement also requires the presence of a clear space around both ends of the sensor in use. Especially in medical applications, such as when placing a sensor on a patient's body for continuous monitoring, the size and lead positions of the sensor are both important issues. Another limitation results from the fact that any displacement of the fusion region necessarily places it under increased tension. At some point of displacement, the tension in the fusion region will become excessive, causing the fusion region to crack or break, with resulting failure of the coupler.

SUMMARY OF THE INVENTION

The present invention provides new variable coupler fiberoptic sensor designs that have comparatively little or no susceptibility to the above described over-tensioning of the fusion region. More particularly, in contrast to the conventional pre-tensioned linear coupler used in prior sensor designs, the present invention utilizes a coupler arrangement that permits deflection of the fusion region without accompanying tension. The coupler may be arranged to have a curved form, for example, which in the most preferred embodiments is substantially U-shaped. By arranging the coupler in a substantially U-shaped form, it also becomes possible to locate the fiberoptic leads adjacent to each other rather than at opposite ends of the sensor, thus avoiding the earlier discussed geometrical limitations inherent in the conventional pre-tensioned linear coupler design.

The present invention also retains the basic advantages of conventional variable coupler fiberoptic sensors relative to other types of fiberoptic sensors and sensors requiring electrically conductive elements at the point of use. Indeed, sensors designed in accordance with the invention may be used to advantage in any application that has heretofore employed conventional variable fiberoptic coupler sensors.

Thus, in one of its various aspects, the present invention provides a fiberoptic sensing apparatus comprising a fiberoptic coupler in which a plurality of optical fibers are joined through a fused coupling region. The optical fibers include at least one input optical fiber and a plurality of output optical fibers, the fiberoptic coupler distributing light incident to the input optical fiber among the plurality of output optical fibers. The apparatus further comprises a support member, and the coupler is mounted to the support member and configured such that at least a portion of the fused coupling region can be deflected without putting the fused coupling region under tension.

In another of its aspects the invention provides a fiberoptic sensing apparatus comprising a fiberoptic coupler in which a plurality of optical fibers are joined through a fused coupling region. The optical fibers include least one input optical fiber and a plurality of output optical fibers, the fiberoptic coupler distributing light incident to the input optical fiber among the plurality of output optical fibers. The apparatus further comprises a support member, and the coupler is mounted to the support member and configured such that the fused coupling region has substantially a U-shape.

Other aspects of the invention will become apparent from a reading of the following description of the preferred embodiments with reference to the accompanying drawings.

DESCRIPTION OF THE PREFERRED EMBODIMENTS

Figure 2:
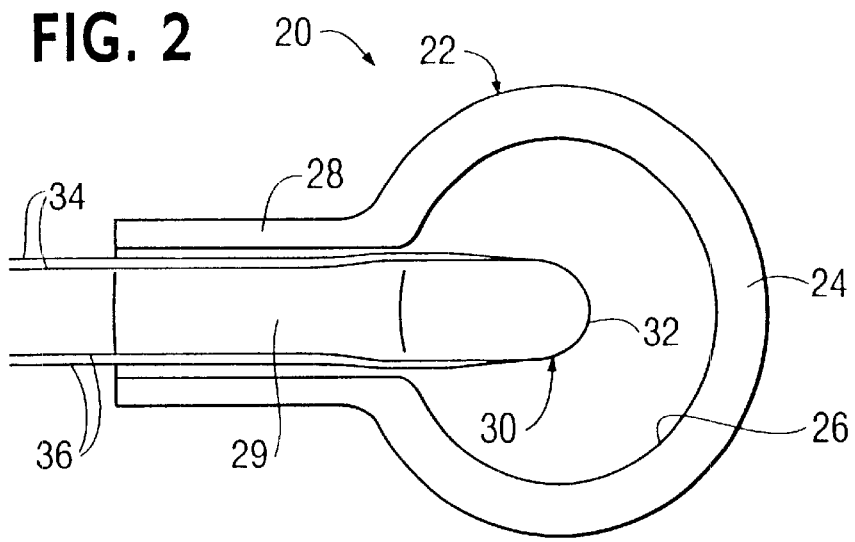
FIG. 2 is a top view of a variable coupler fiberoptic sensor according to the invention, being designed for monitoring cardiovascular sounds such as from the wrist or the chest.
Figure 3:
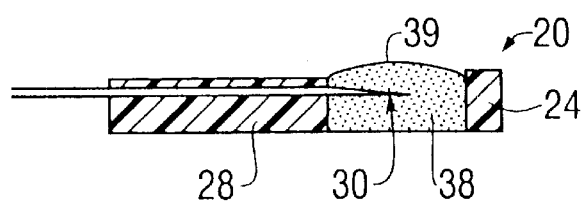
FIG. 3 is a sectional side view of the sensor of FIG. 2.

FIGS. 2 and 3 of the accompanying drawings show an example of a variable coupler fiberoptic sensor 20 in accordance with the invention. The sensor is constructed for placement against a medical patient's body, such as on the chest or wrist, for sensing cardiovascular sounds including both audible and sub-audible sounds from the heart, pulse, and circulatory system.

The sensor 20 comprises a support member 22 having a generally circular head portion 24, which is provided with a central well or through hole 26, and a handle-like extension 28. A biconical fused tapered coupler 30 is mounted to the support member with at least a portion (here, the entirety) of its fused coupling region 32 disposed in the space 26 and arranged in a U-shape. Input fiber leads 34 and output fiber leads 36 of the coupler are disposed beside one another in a channel 29 formed in the extension 28. The leads are manipulated so as to bend the coupling region 32 through 180° into the desired shape and then secured within the channel by a suitable adhesive, such as an epoxy-based glue. The coupling region, which is not under tension, may be potted by filling the space 26 with elastomer to form a sensing membrane 38 (not shown in FIG. 2) in the known manner—for example, by filling with a silicone rubber such as GE RTV 12. Alternatively, as will be seen hereinafter, the coupling region may be coated with a layer of coating material such as GE SS 4004 (polydimethylsiloxane with methyl silsesquioxanes) to eliminate the need for potting. This material is normally used as a primer for bonding room temperature vulcanizing (RTV) materials to surfaces that would otherwise form weak bonds. The advantage of eliminating the potting is that the sensitivity is increased, because the potting tends to reduce sensitivity no matter how thinly it is applied. Support member 22 is suitably formed of a moldable plastic, such as Plexiglass®, polyvinyl chloride (PVC), or other suitable materials known in the art.

As shown in FIG. 3, the upper portion of the membrane 38 has a convex surface 39 that protrudes from the plane of the support structure for contacting the patient's body. The convex configuration of the contact surface makes the sensor more of a point probe to better localize the cardiovascular sounds being monitored. In a practical embodiment of the sensor, the maximum diameter of the membrane may be about the same as that of a nickel with the contact surface protruding by about half that amount, but the membrane may be smaller or larger as desired to suit a particular application. The support plate dimensions may be any convenient size, so long as the coupler fusion region and the fiber portions near the fusion region are securely supported. The sensitivity of the device is dependent upon the stiffness of the membrane, as in prior devices. Using softer or stiffer membrane materials will provide different sensitivities to the readings received from the body coupling.

When the contact surface 39 is placed upon a patient's body, as at the chest or wrist, the membrane 38 couples skin displacements associated with cardiovascular sounds to the coupling region 32 of the fiberoptic coupler 30. The coupling region is thereby deflected, changing the light output ratio of the output fibers 36 in accordance with the sounds being monitored.

Figure 4:
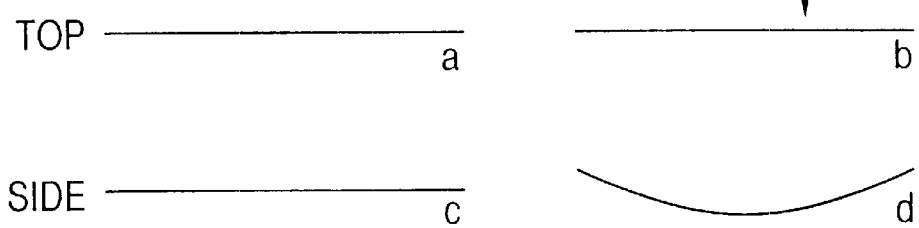
FIG. 4 shows explanatory views (Views 4a–4d) of normal and deflected states of the fusion region of a conventional pre-tensioned linear coupler.
Figure 5:
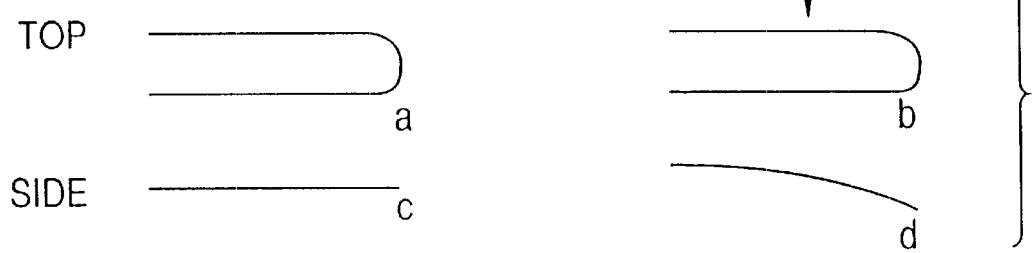
FIG. 5 shows corresponding explanatory views (Views 5a–5d) for a U-shaped fusion region in accordance with the principles of the invention.

FIGS. 4 and 5 provide a pictorial comparison between the deflection of a conventional pre-tensioned linear fiberoptic coupler and the deflection of the U-shaped coupler in the sensor of FIGS. 2 and 3. Views 4a and 4c are top and side views, respectively, showing the fusion region of the conventional coupler in its normal state. Views 4b and 4d are corresponding views of the fusion region being deflected by a downward force F. Views 5a–5d in FIG. 5 are corresponding views to FIG. 4, but show the U-shaped coupler employed in the present invention.

As will be appreciated from View 4d, the deflection of the fusion region in the conventional coupler causes a bowing that tends to stretch and thereby increase the tension on the fusion region. By contrast, the deflection of the U-shaped fusion region in View 5d, which is seen to occur along a direction perpendicular to the plane of the U-shape, merely causes a flexing of the U along its height (horizontal dimension in View 5d), with the fusion region being under substantially no tension. Thus, even large displacements of the fusion region will not cause cracking or breaking.

In the practice of the present invention, the fusion region of the fiberoptic coupler need not be U-shaped or even substantially so. Any configuration of the fusion region that allows for deflection without tensioning of the fusion region may be used. For example, arcuate shapes, parabolic and hyperbolic shapes with widely divergent sides, and other curved shapes may be used. A substantially U-shaped form may be preferred, however, because such a form allows positioning of the coupler input and output leads on the same side of the sensor, resulting in a compact design that does not require clearances to accommodate leads at opposite ends of the structure. A substantially U-shaped form also produces significant increases in sensitivity, linearity, and dynamic range as compared with the conventional linear couplers. Other shapes, such as those mentioned above, may also produce these advantages. The length of the fusion region may be established during production as previously explained, and in actual sensors constructed in accordance with the invention has typically been about 1.5 cm.

Figure 1:
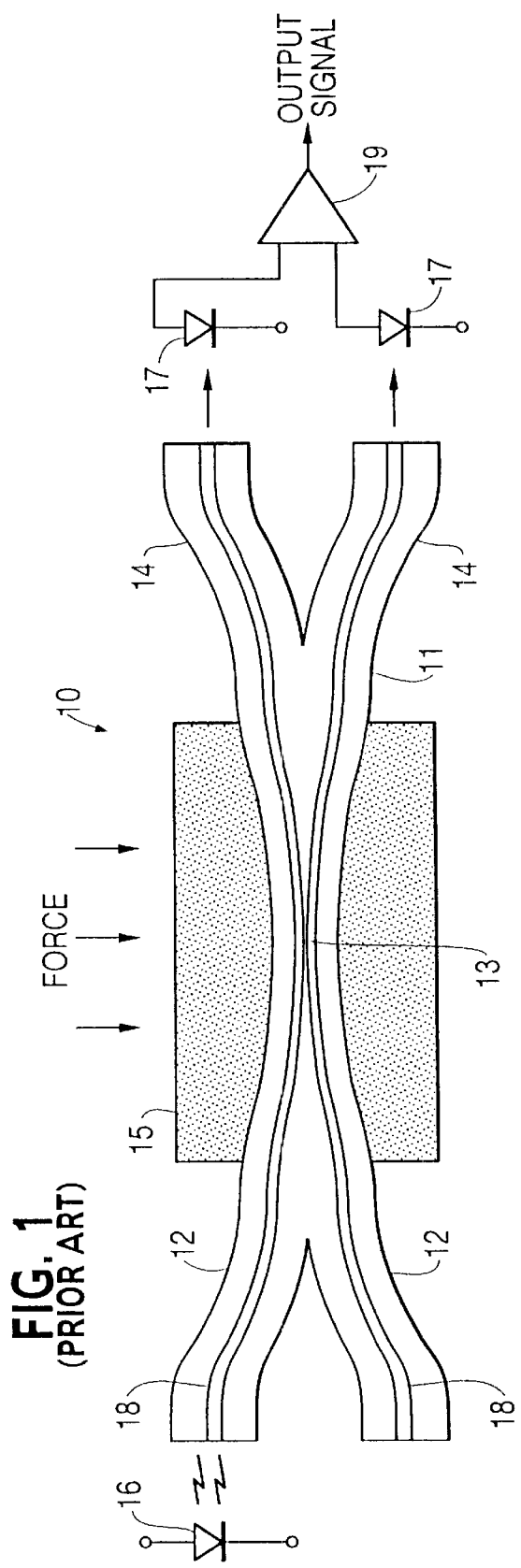
FIG. 1 illustrates the basic construction of a conventional variable coupler fiberoptic sensor.
Figure 6:
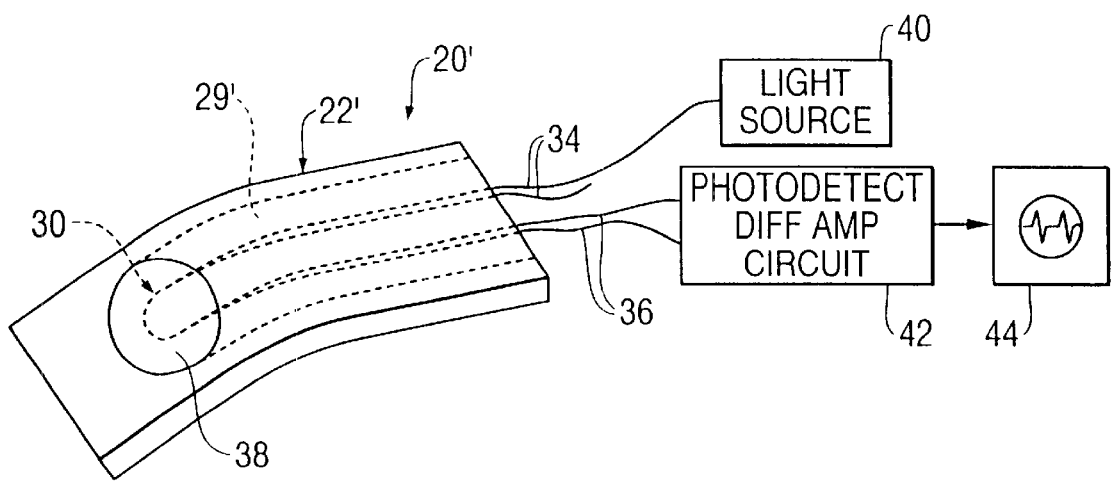
FIG. 6 shows a fiberoptic wrist sensing apparatus according to the invention.

FIG. 6 shows another variable coupler fiberoptic sensor 20' in accordance with the invention. The sensor has the same basic structure as that of the previous embodiment, except that the support member 22' is formed as a substantially rectangular plate angled at about 30° to conform to the human wrist anatomy and facilitate wearing of the sensor by the patient, as by strapping the sensor to the wrist. As also shown in FIG. 6, one of the input leads 34 is optically coupled to a light source 40 (e.g., and LED or semiconductor laser) and the output fibers 36 are optically coupled to a photodetection/differential amplifier circuit 42, as previously described in connection with FIG. 1. The differential amplifier circuit may be coupled to an oscilloscope 44 or some other form of display device, such as a personal computer, to display the output of the differential amplifier circuit. If appropriate to a particular application, the support member may house the light source 40, the differential amplifier circuit 42, and radio transmitting device (not shown) coupled to the differential amplifier circuit to provide for remote monitoring. Indeed, such provision can be made in any of the sensor structures of the invention described herein.

Figure 7:
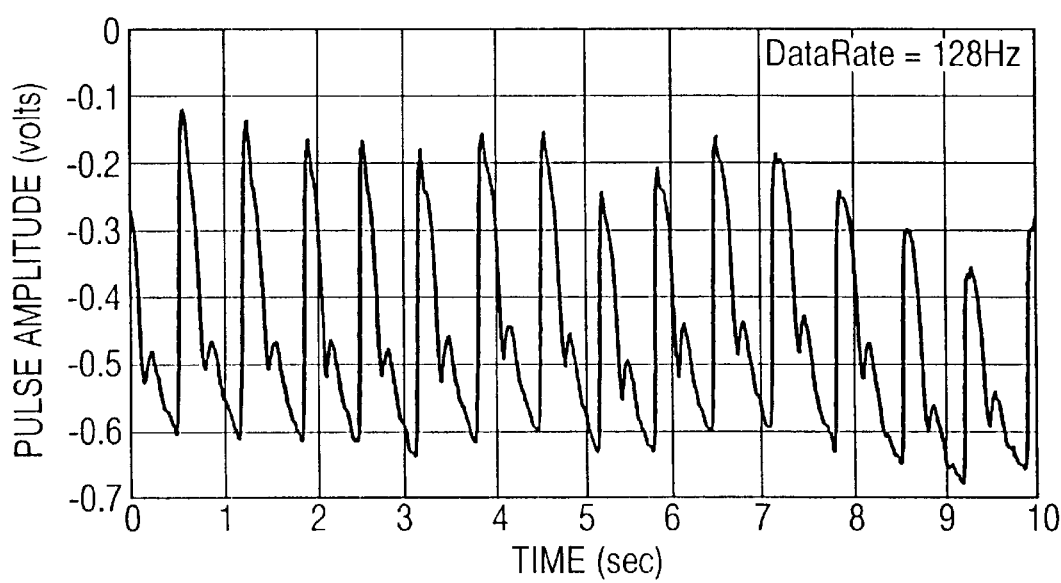
FIG. 7 is a graph depicting the response of the wrist sensor in the apparatus of FIG. 6 to pulsations of the wrist.

FIG. 7 shows the wrist heartbeat/breathing signal obtained from a human subject with the sensor 20' of FIG. 6. The data stream in FIG. 7 was obtained at a sampling rate of 128 samples per second. It will be appreciated that the pulse waveform, as read by the sensor, is a more complex phenomenon than standard pulse readings. The pulse waveform exhibits the amplitude structure of the pulse as a function of time. The amplitude structure of the pulse is not what is "felt" as an impulse function by a finger at a pulse point, although that function is present. Within the amplitude structure, there are all of the heart sounds as well as information on breathing and other indicators of physical condition. The sensitivity achieved with sensors according to the present invention makes them very good at sensing the complex pulse waveform.

Figure 8:
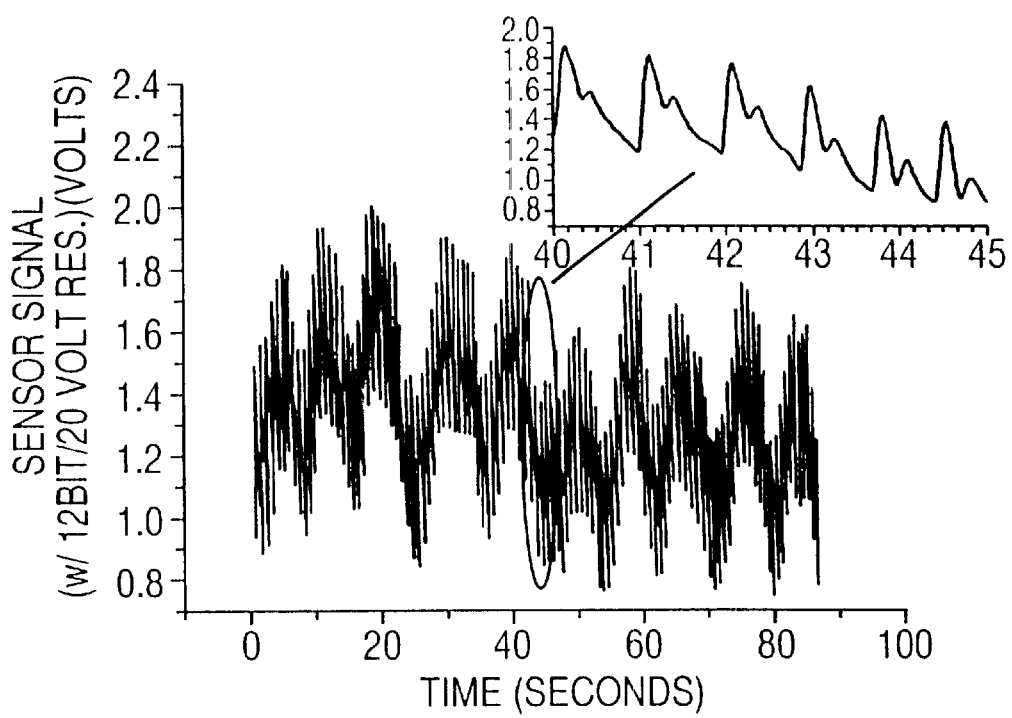
FIG. 8 is another graph of the sensor response at the wrist.

FIG. 8 shows another wrist heartbeat/breathing signal obtained from a human subject with the sensor 20'. Here, the data stream was digitized using a 12-bit A/D converter at a sampling rate of 64 samples per second. The heartbeat signal is very well resolved, as the inset graph demonstrates. In addition, the modulation introduced by the breathing cycle is clearly visible over the course of the 84 second run.

Figures 9, 10:
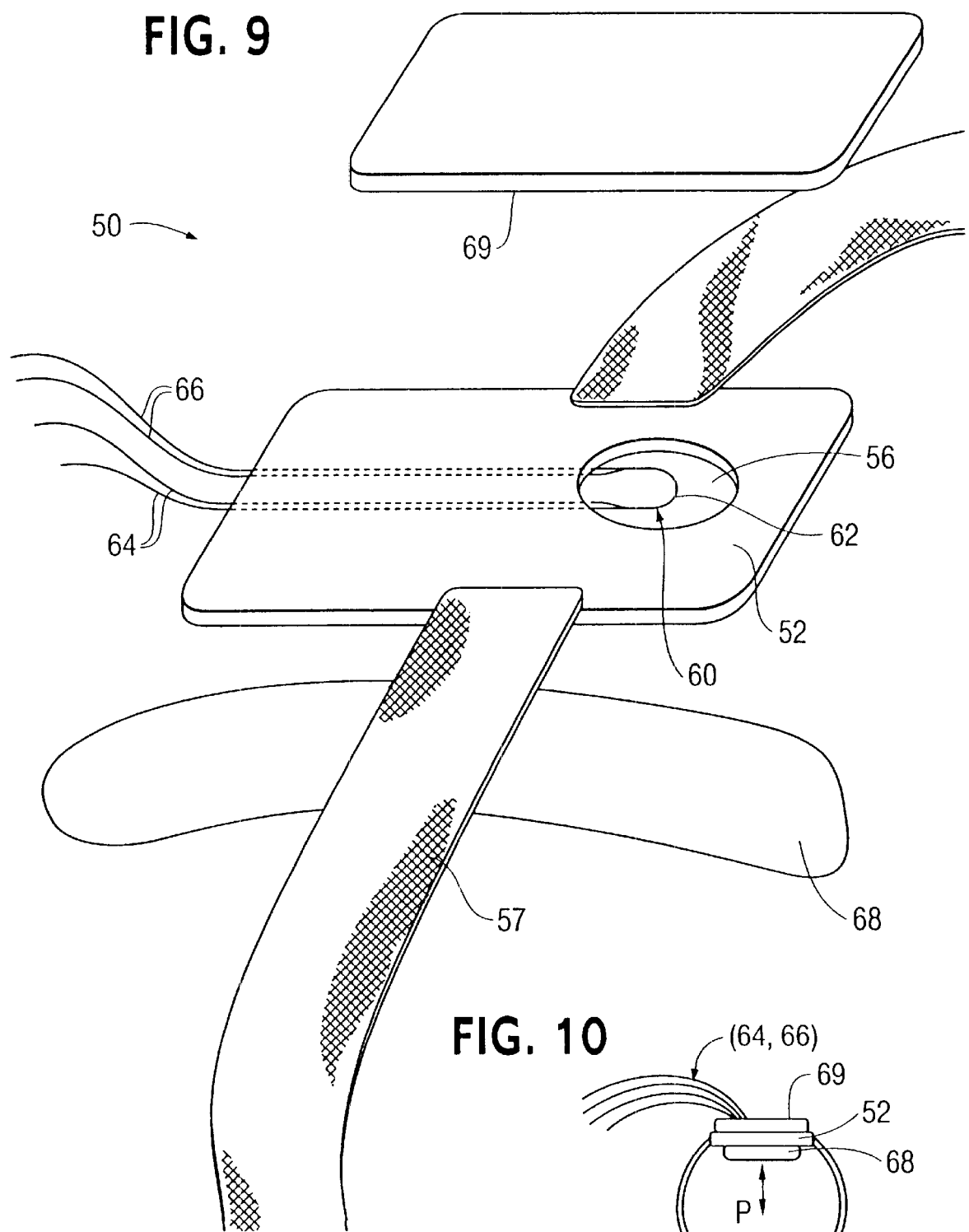
FIG. 9 is an exploded view of another wrist sensor according to the invention.
FIG. 10 is an end view of the FIG. 9 sensor in assembled form.

FIGS. 9 and 10 show another embodiment of the invention, applied to a wrist sensor 50. In this embodiment, the fusion region 62 of the fiberoptic coupler is not potted, but coated as previously discussed in connection with FIG. 1. The fusion region 62 is coupled to pulsations of the wrist (denoted by arrow P) by a fluid- or gel-filled elastic pillow 68. The fiberoptic coupler is mounted to a support plate 52 similar to that of FIG. 6, except that the support plate 52 is planar, not angled (the channel for the input and output leads 64, 66 having been omitted from illustration for simplicity). The support plate is secured to the top side of pillow 68 and a cover 69 is attached to the top side of the support plate to protect the fusion region 62 of the coupler 60 at the hole 56. The hole 56 allows the hydraulic pressure of the pulse activity to push on and deflect the fusion region by virtue of the contact between the fusion region and the upper surface of the pillow 68 which, due to its flexibility, protrudes into the hole 56 to contact the coupler fusion region. A wrist strap 57 attached to the support plate 52, as by glue, allows the sensor to be secured to the wrist. Reference numbers 64 and 66 denote the input fibers and output fibers, respectively.

The unpotted sensor design of FIGS. 9 and 10 is advantageous over the potted designs previously described, because the absence of the sensing membrane results in greater sensitivity. Also, unlike the bent design in FIG. 6, the planar configuration of the support plate does not require out-of-plane bending of the coupler leads, which causes a reduction of light intensity. Instead, the coupler s maintained in a planar configuration, which optimizes the light intensity in the system.

Figure 11:
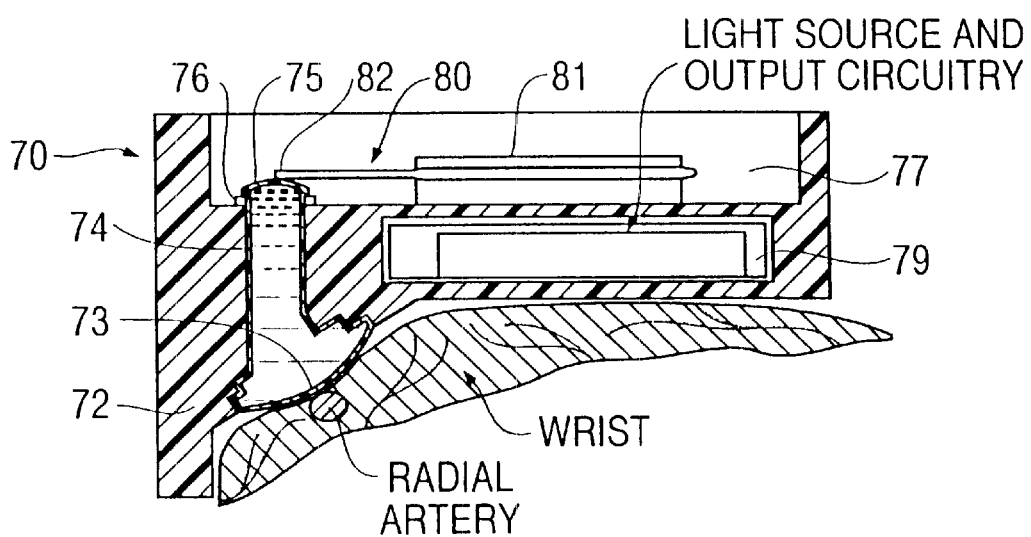
FIG. 11 illustrates another wrist sensor according to the invention, shown in section as worn on the wrist.

FIG. 11 shows still another embodiment of the invention, applied to a wrist sensor 70 shown in cross-section as worn on the wrist. The sensor includes a frame member 72 having an inner configuration which conforms generally to the wrist, as shown. The frame member may be constructed from any suitable material, preferably a plastic such as Delrin®, PVC, acrylic, Lucite®, Plexiglass®, styrene, or other polymers.

An upper portion of the frame provides a chamber 77 for housing the fiberoptic coupler 80 and its support plate 81. Since the coupler is housed by the frame member, the support plate, which is channeled to receive the input and output leads, need not include an opening (e.g., a well or through hole) to house the fusion region 82 of the coupler as in previous embodiments. The fusion region is coated, rather than potted, as previously described. The support plate 81, which may be of the same material as the frame 72, and the coupler are assembled as a module and glued in place in the chamber 77. The chamber is closed by a protective cover plate (not shown).

To couple the fusion region to the pulsations of the radial artery, a fluid column 74 is provided. The column has a pair of resilient membranes 73 and 75 provided at its inner and outer ends, respectively, and extends through the thickness of the frame 72 between the chamber 73 and the frame inner surface. The coupler module is installed with the coupler fusion region 82 in contact with the outer membrane 75 of the fluid column. The outer membrane is attached to an annular boss 76 to raise the height of the fluid column for contact with the coupler fusion region. The contact with the outer membrane may subject the fusion region to a slight pre-load. The coupler may be manufactured such that the pre-loading of the fusion region will produce a substantially equal division of light between the output fibers, thus providing a more linear dynamic range. The inner portion (lower portion in FIG. 11) of the fluid column is stepped as shown, so as to increase the diameter of the coupling area at the wrist.

The membranes constitute an important part of the fluid column. Since the arterial pulsations are weak, the membranes should be light, thin, and of low durometer and high extensibility for optimum performance. At the same time, at least the inner membrane should be rugged enough to endure continuous contact with the skin. A material found to have excellent characteristics for the membrane is FlexChem, an FDA-approved, highly durable, vinyl based material available in pellet form from Colorite. FlexChem is also thermomoldable, which permits the inner sensing membrane 73 to be molded to provide maximum coupling area with the radial artery and to protrude from the inner surface of the frame member 72 for better coupling with the wrist.. A compatible fluid for use with FlexChem membranes is medical grade MDM silicone fluid available from Applied Silicone Corp. Water, incidentally, is not preferred for use with FlexChem membranes since the membranes are permeable to water vapor.

Several inner membrane sizes were tested to determine the effect on sensor response. In particular, membrane diameters of 4 mm, 7 mm, and 10 mm were tested for response to driven-oscillator stimuli calibrated using a commercial accelerometer. The response was examined over a frequency range of 0 to about 11 Hz (cardiovascular and breathing signals are typically in the range from 0.1 to 4 Hz). Each of the membranes provided acceptable response, with the 10 mm membrane providing the best response.

Returning to FIG. 11, the present embodiment also demonstrates how ancillary components, such as the light source and output circuitry (e.g., photodetectors and differential amplifier circuitry) may be incorporated into the sensor unit. More particularly, such components may be housed in one (as shown) or more internal chambers 79 of the frame 72.

Figure 14:
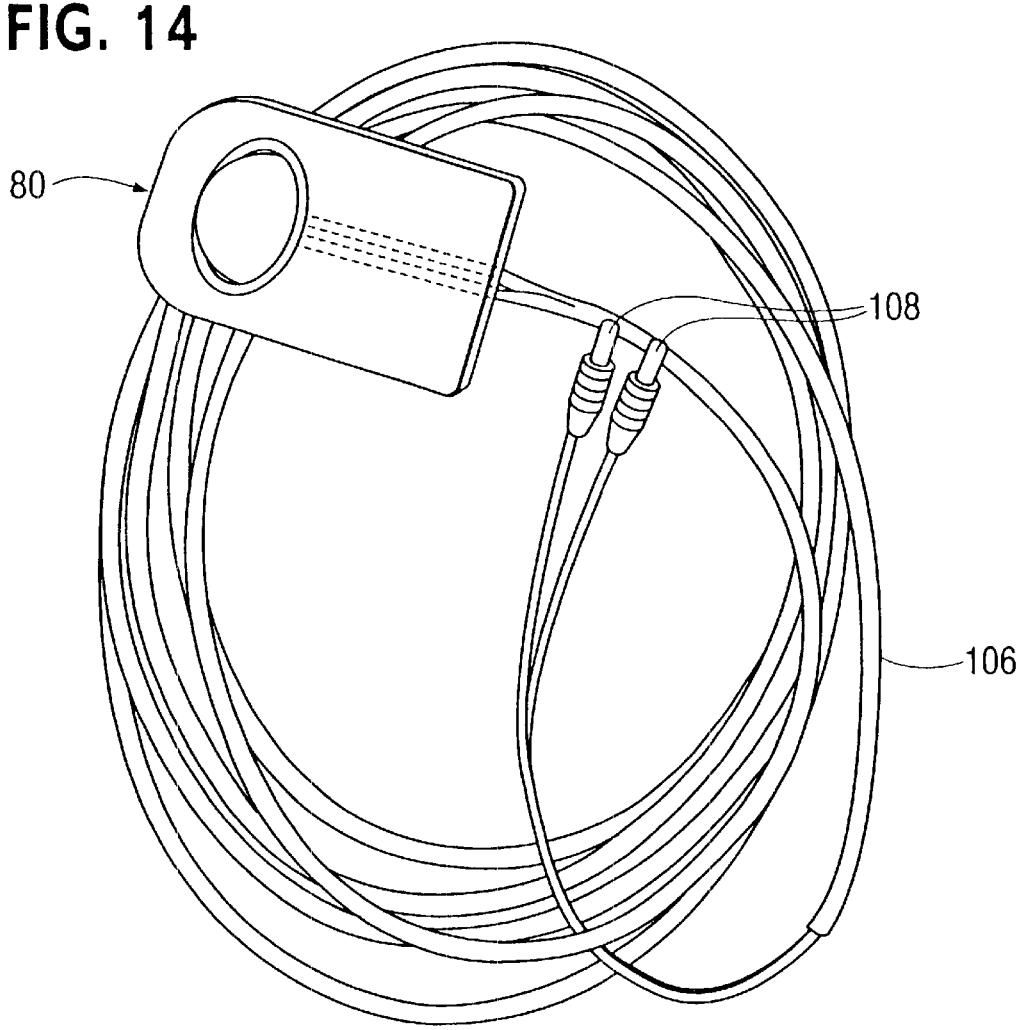
FIG. 14 is a perspective view showing the FIG. 12 sensor and its fiberoptic leads with installed connectors.
Figure 12:
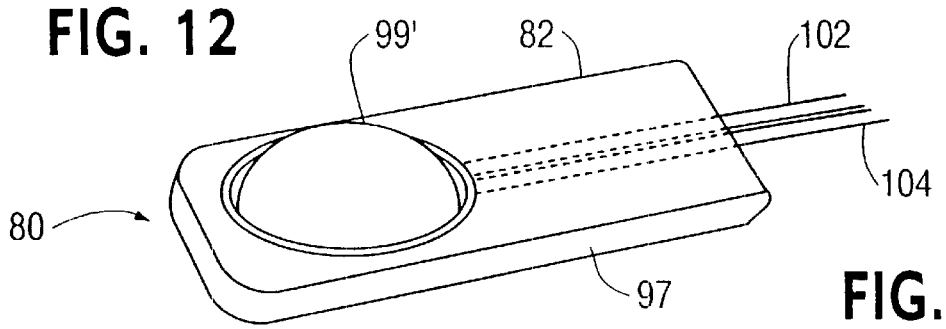
FIG. 12 is a perspective view of a carotid artery sensor according to the invention.
Figure 13:
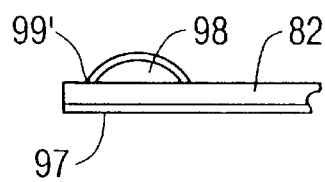
FIG. 13 is a fragmentary side elevation of the FIG. 12 sensor.

FIGS. 12–14 illustrate another embodiment of the invention, applied to a sensor 80 for the carotid artery. This sensor uses a planar, channeled support plate 82 and coupler arrangement similar to that of FIG. 9, except that the fusion region is potted to provide a sensor membrane. The membrane area may be made sufficiently large (e.g., about the size of a quarter dollar) to allow for the addition of a spherical cap 99' over the convexly protruding surface of the sensing membrane 98. The addition of the spherical cap renders the sensor less sensitive to any rocking motion caused by the hand when the sensor is manually pressed against the neck. The coupler is protected at the back side (bottom in FIGS. 12 and 13) of the sensor by a plastic cover plate 97. The sensor may be secured to the neck by any suitable means, such as adhesive tape.

The input and output fibers are encased as pairs in respective protective sheaths 102 and 104, which in turn are encased in an outer protective sheath 106. Fiberoptic connectors 108 are provided at the ends of the leads to interface the sensor with external components.

It should be noted that the optical fiber used in the sensors of the present invention is most preferably of very high quality, such as Corning SMF28 which exhibits an optical loss of about 0.18 dB per Km. The photodetectors may be gallium-aluminum-arsenide or germanium detectors for light wavelengths above 900 nm and silicon detectors for shorter wavelengths.

The photodetectors may be connected in either a photovoltaic mode or a photoconductive mode. In the photovoltaic mode, transimpedance amplifiers (which convert current to voltage) may be used to couple the detectors to the differential amplifier inputs. The transimpedance amplifier outputs may also be filtered to eliminate broadband noise. As another example, the transimpedance amplifier outputs could be fed directly to a digital signal processor (DSP), where subsequent filtering and processing could be accomplished digitally through programmed algorithms. A DSP having transimpedance inputs would, of course, eliminate the need for discrete transimpedance amplifiers in the preceding example. In the photoconductive mode, the detector outputs can be connected to a conventional voltage amplifier. This approach results in more noise, but may be used in applications where cost is a major concern and a lower noise level is not.

It is to be understood, of course, that the foregoing embodiments of the invention are merely illustrative and that numerous variations of the invention are possible in keeping with the invention as more broadly described herein.

What is claimed is:

1. Fiberoptic sensing apparatus, comprising:
    a fiberoptic coupler in which a plurality of optical fibers are joined through a fused coupling region, said optical fibers including at least one input optical fiber and a plurality of output optical fibers, said fiberoptic coupler distributing light incident to said input optical fiber among said plurality of output optical fibers; and
    a support member;
    said coupler being mounted to said support member and configured such that at least a portion of said coupling region is curved and can be deflected to change the light distribution among said output fibers with said coupling region being under substantially no tension.

2. Fiberoptic sensing apparatus according to claim 1, wherein said portion of said coupling region lies substantially on a plane.

3. Fiberoptic sensing apparatus according to claim 2, wherein said deflection is along a direction perpendicular to said plane.

4. Fiberoptic sensing apparatus according to claim 2, further comprising a resilient member having a surface to be displaced in response to forces fiberoptic sensed by the sensing apparatus, said surface being disposed adjacent to said portion of said coupling region in a direction perpendicular to said plane and displaceable along said direction in order to deflect said portion of said coupling region along said direction in response to said forces.

5. Fiberoptic sensing apparatus according to claim 4, wherein said input and output optical fibers are single mode optical fibers.

6. Fiberoptic sensing apparatus according to claim 1, wherein said support member has a surface with channel portions in which said input and output fibers are received, and part of said coupler including said portion of said coupling region extends from said channel portions.

7. Fiberoptic sensing apparatus according to claim 6, wherein said support member has an opening in communication with said channel portions and in which said portion of said coupling region is received.

8. Fiberoptic sensing apparatus according to claim 7, wherein said support member is a plate member.

9. Fiberoptic sensing apparatus according to claim 8, wherein said plate member is planar.

10. Fiberoptic sensing apparatus according to claim 8, wherein said plate member is configured to conform generally with a wrist of a patient.

11. Fiberoptic sensing apparatus according to claim 7, wherein said portion of said coupling region is encapsulated in a body of resilient material.

12. Fiberoptic sensing apparatus according to claim 11, wherein said body of resilient material protrudes convexly outwardly from said opening.

13. Fiberoptic sensing apparatus according to claim 1, wherein said support member is disposed on a frame member configured to conform generally with a wrist of a patient, said frame member being provided with a fluid column having a first portion with a membrane disposed to receive pulsations from a radial artery at the wrist of the patient and a second portion having a membrane to which said pulsations are transmitted via the fluid and which is disposed to transmit motion of said pulsations to said portion of said coupling region.

14. Fiberoptic sensing apparatus according to claim 13, wherein said portion of said coupling region rests on said membrane of said second portion of said fluid column.

15. Fiberoptic sensing apparatus according to claim 1, further comprising an electro-optic circuit optically coupled to said plurality of output fibers to convert light received from said output fibers to an electrical output having a level dependent upon an amount of deflection of said portion of said coupling region.

16. Fiberoptic sensing apparatus according to claim 15, wherein said electro-optic circuit comprises a plurality of photodetectors optically coupled to said plurality of output fibers, respectively, and a differential amplifier circuit to which outputs of said photodetectors are connected.

17. Fiberoptic sensing apparatus according to claim 16, further comprising a display device connected to an output of said electro-optic circuit.

18. Fiberoptic sensing apparatus according to claim 15, wherein said input and output optical fibers are single mode optical fibers.

19. Fiberoptic sensing apparatus according to claim 1, wherein said support member is a plate member.

20. Fiberoptic sensing apparatus according to claim 19, wherein said plate member is planar.

21. Fiberoptic sensing apparatus according to claim 19, wherein said plate member is configured to conform generally with a wrist of a patient.

22. Fiberoptic sensing apparatus according to claim 1, wherein said portion of said coupling region is encapsulated in a body of resilient material.

23. Fiberoptic sensing apparatus according to claim 22, wherein said body of resilient material has a convex surface disposed to be coupled to movement of an external medium.

24. Fiberoptic sensing apparatus according to claim 1, wherein said support member is constructed to conform generally with a wrist of a patient.

25. Fiberoptic sensing apparatus according to claim 1, further comprising a gel coupling or a fluid coupling to couple said coupling region to movement of an external medium.

26. Fiberoptic sensing apparatus according to claim 1, wherein said input and output optical fibers are single mode optical fibers.

27. Fiberoptic sensing apparatus, comprising:
    a fiberoptic coupler In which a plurality of optical fibers are joined through a fused coupling region, said optical fibers including at least one input optical fiber and a plurality of output optical fibers, said fiberoptic coupler distributing light incident to said input optical fiber among said plurality of output optical fibers; and
    a support member;
    said coupler being mounted to said support member and configured such that said fused coupling region has substantially a U-shape of which at least a portion can be deflected to change the light distribution among said output optical fibers.

28. Fiberoptic sensing apparatus according to claim 27, wherein said support member has a surface with channel portions in which said input and output fibers are received, and part of said coupler including said coupling region extends from said channel portions.

29. Fiberoptic sensing apparatus according to claim 28, wherein said support member has an opening in communication with said channel portions and in which said coupling region is received.

30. Fiberoptic sensing apparatus according to claim 29, wherein said support member is a plate member.

31. Fiberoptic sensing apparatus according to claim 30, wherein said plate member is planar.

32. Fiberoptic sensing apparatus according to claim 30, wherein said plate member is configured to conform generally with a wrist of a patient.

33. Fiberoptic sensing apparatus according to claim 29, wherein said coupling region is encapsulated in a body of resilient material.

34. Fiberoptic sensing apparatus according to claim 33, wherein said body of resilient material protrudes convexly outwardly from said opening.

35. Fiberoptic sensing apparatus according to claim 27, wherein said support member is disposed on a frame member configured to conform generally with a wrist of a patient, said frame member being provided with a fluid column having a first portion with a membrane disposed to receive pulsations from a radial artery at the wrist of the patient and a second portion having a membrane to which said pulsations are transmitted via the fluid and which is disposed to transmit motion of said pulsations to said coupling region.

36. Fiberoptic sensing apparatus according to claim 35, wherein a portion of said coupling region rests on said membrane of said second portion of said fluid column.

37. Fiberoptic sensing apparatus according to claim 27, further comprising an electro-optic circuit optically coupled to said plurality of output fibers to convert light received from said output fibers to an electrical output having a level dependent upon an amount of deflection of said coupling region.

38. Fiberoptic sensing apparatus according to claim 37, wherein said electro-optic circuit comprises a plurality of photodetectors optically coupled to said plurality of output fibers, respectively, and a differential amplifier circuit to which outputs of said photodetectors are connected.

39. Fiberoptic sensing apparatus according to claim 38, further comprising a display device connected to an output of said electro-optic circuit.

40. Fiberoptic sensing apparatus according to claim 37, wherein said input and output optical fibers are single mode optical fibers.

41. Fiberoptic sensing apparatus according to claim 27, wherein said support member is a plate member.

42. Fiberoptic sensing apparatus according to claim 41, wherein said plate member is planar.

43. Fiberoptic sensing apparatus according to claim 41, wherein said plate member is configured to conform generally with a wrist of a patient.

44. Fiberoptic sensing apparatus according to claim 27, wherein said portion of s aid coupling region is encapsulated in a body of resilient material.

45. Fiberoptic sensing apparatus according to claim 44, wherein said body of resilient material has a convex surface disposed to be coupled to movement of an external medium.

46. Fiberoptic sensing apparatus according to claim 27, wherein said support member is constructed to conform generally with a wrist of a patient.

47. Fiberoptic sensing apparatus according to claim 27, further comprising a gel coupling or a fluid coupling to couple said coupling region to movement of an external medium.

48. Fiberoptic sensing apparatus according to claim 27, wherein said coupler is mounted to said support member such that said coupling region lies substantially on a plane and can be deflected transversely to said plane by flexing thereof along a height of said U-shape.

49. Fiberoptic sensing apparatus according to claim 48, wherein said input and output optical fibers are single mode optical fibers.

50. Fiberoptic sensing apparatus according to claim 27, wherein said coupler is mounted to said support member such that said coupling region lies substantially on a plane, and further comprising a resilient member having a surface to be displaced in response to forces sensed by the fiberoptic sensing apparatus, said surface being disposed adjacent to said coupling region in a direction perpendicular to said plane and displaceable along said direction to deflect a portion of said coupling region along said direction in response to said forces.

51. Fiberoptic sensing apparatus according to claim 50, wherein said input and output optical fibers are single mode optical fibers.

52. Fiberoptic sensing apparatus according to claim 27, wherein said input and output optical fibers are single mode optical fibers.

* * * * *